(12) United States Patent
Teichtmann et al.

(10) Patent No.: US 8,668,711 B2
(45) Date of Patent: Mar. 11, 2014

(54) MEDICAL INSTRUMENT WITH A FLEXIBLE SEALING SYSTEM VIA SPHERICAL HEADS

(71) Applicants: Elmar Teichtmann, Bretten (DE); Michael Sauer, Tuttlingen (DE)

(72) Inventors: Elmar Teichtmann, Bretten (DE); Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 13/908,685

(22) Filed: Jun. 3, 2013

(65) Prior Publication Data

US 2013/0267900 A1    Oct. 10, 2013

Related U.S. Application Data

(62) Division of application No. 12/507,476, filed on Jul. 22, 2009, now Pat. No. 8,475,485.

(30) Foreign Application Priority Data

Jul. 23, 2008 (DE) .......................... 10 2008 035 310

(51) Int. Cl.
*A61B 17/34* (2006.01)

(52) U.S. Cl.
USPC .......................................... 606/185; 604/256

(58) Field of Classification Search
USPC ......... 606/167, 185; 604/164.01, 164.03, 256
See application file for complete search history.

(56) References Cited

U.S. PATENT DOCUMENTS

| 5,603,702 | A | | 2/1997 | Smith et al. |
| 5,628,732 | A | * | 5/1997 | Antoon et al. ........... 604/167.06 |
| 6,063,063 | A | * | 5/2000 | Harboe et al. ................ 604/256 |
| 2008/0065116 | A1 | | 3/2008 | Lee et al. |

FOREIGN PATENT DOCUMENTS

| DE | 4306205 C1 | 10/1994 |
| EP | 0696459 A1 | 2/1996 |
| EP | 0594687 B1 | 4/1998 |
| WO | 2007121425 A1 | 10/2007 |

OTHER PUBLICATIONS

European Search Report; Application No. EP 09 16 6106; Apr. 23, 2010; 4 pages.

* cited by examiner

*Primary Examiner* — Victor Nguyen
(74) *Attorney, Agent, or Firm* — St. Onge Steward Johnston & Reens LLC

(57) ABSTRACT

A medical instrument has a cannula and a seal disposed in the cannula. An expansion device serves for expanding an opening in the seal for guiding shafts of other instruments of greater diameter in a sealed manner through the expanded opening. The expansion device has an expansion cone with a plurality of slats mounted pivotably on an annular body at a first end thereof, a second end of the slats being connected to the seal in an area of the opening. The slats are connected at its first ends to the annular body via spherical heads engaged into corresponding openings in the annular body.

25 Claims, 11 Drawing Sheets

MEDICAL INSTRUMENT WITH A FLEXIBLE SEALING SYSTEM VIA SPHERICAL HEADS

The present indention relates to a medical instrument, with a cannula through which shafts of other instruments having different shaft diameters can be guided, with a seal comprising an opening with a variable opening cross section through which the shafts having different shaft diameters can be guided sealingly, with an expansion device for expanding the opening of the seal, which expansion device has an expansion cone with a plurality of slats that are mounted pivotably on at annular body and form an expansion body that narrows from the proximal end to she distal end and that is connected to the seal in the area of the opening.

A medical instrument of this kind is known from EP 0 696 459 B1.

Said medical instrument is a trocar that is used in minimally invasive surgery. The trocar is introduced through a small opening, which can be formed by a small incision for example, through the abdominal wall into the abdominal cavity of the patient by means of a trocar mandrel. After removal of the trocar mandrel, shafts of other instruments used for the surgical intervention are then passed through this trocar. These instruments include, for example, gripping tools, coagulation instruments, endoscopes and the like. These have different diameters.

Since minimally invasive interventions of this kind are often performed during insufflation of the internal cavity in which the operation takes place, all the intervention points must be gas-tight.

In the aforementioned EP 0 696 459 B1, this purpose is served by an elastic conical seal that is arranged in the trocar and that narrows from the proximal end to the distal end. To permit uniform widening of the seal when an instrument is inserted into the trocar, the expansion cone is arranged in the proximal direction from this seal. An instrument inserted into the expansion cone expands the latter radially, which widens the opening in the seal. In addition to permitting easier widening of the seal, the expansion cone also prevents damage to the seal during insertion of sharp-edged instruments, because it can be made of a hard material. In this way, the seal is protected by the expansion cone.

To construct the expansion cone, the slats are mounted pivotably at a first end thereof on a ring, as a result of which the cortical body of the expansion cone is obtained and the slats can be pivoted radially. For this purpose, they have axial pins at one end, with which the slats have to be engaged pivotably in corresponding recesses in the annular body.

For this purpose, each slat therefore requires exactly shaped end pieces with axial pins. Correspondingly, the annular body must also have exactly shaped engagement means, in addition to which an exactly shaped cover has to be fitted onto the device in order to ensure that the slats do not fall off from the ring. The construction therefore requires a number of exactly produced individual parts with relatively complicated details. This is difficult, especially because of the small size of the components, in the millimeter range, and therefore makes construction complicated. The same also applies to the assembly work in which the very small axial pins have to be engaged in the corresponding recesses in the annular body.

It is therefore an object of the present invention to develop a medical instrument of this kind in such a way that the sealing system is of simpler construction and is less complicated to assemble and less expensive to produce.

SUMMARY OF THE INVENTION

According to the invention, the object is achieved, on the one hand, by the fact that the slats are connected to the annular body via film hinges.

The pivotable connection between slats and annular body by means of film hinges allows the expansion cone to be made as a single workplace by injection moulding. The work involved in producing the expansion cone is thus greatly reduced, since only a single part has to be manufactured and there is no need for individual parts to be assembled. This saves time and reduces costs.

According to the invention, the object is achieved, on the other hand, by the fact that the slats have spherical heads via which they can be engaged in corresponding openings in the annular body.

Although the expansion cone in this solution is composed of several parts, the provision of spherical heads, which have to be fitted into the corresponding openings of the annular body, represents a simple design measure. No particular attention has to be paid to fitting the spherical heads into the openings in the annular body, as a result of which the assembly is made simple.

In one embodiment, the spherical heads of the slats are held in the annular body by a cover ring.

The use of a cover ting presents the slats, mounted via their ball joints, from falling out of the annular body. It further supports the concept of simple construction, since the cover ring ensures a secure hold of the slats, mounted via their ball joints.

In another embodiment, the seal extends in the distal direction away from the distal end of the expansion core.

For it, the seal can be designed as a pot-seal, a bottom of said pot-seal is connected to said distal end of said expansion cone.

The choice of this structural arrangement has the advantage, on the one hand, that joining together the expansion cone and the seal is simple, since both components are connected to each other via easily accessible outer races. On the other hand, the resulting arrangement of the seal facilitates the removal of tissue samples, since it in this way has a funnel-like shape that narrows from the pedal end to the proximal end. If, for example, such a sample is taken hold of by a gripping tool and is then guided through the trocar sleeve in the proximal direction, it finally reaches the seating system. There, by virtue of the gradually decreasing diameter of the seal it is guided to the proximal narrow opening of the seal and, if appropriate, also adapted in shape. This avoids an undesirable situation in which the sample, during its removal, becomes caught because of an abrupt change in diameter.

In another embodiment of the invention, the seal surrounds the expansion cone.

For it, the seal can be designed as a pot-seal wherein said expansion cone is arranged within said pot-seal, and a distal end of said expansion cone is connected to said opening in a bottom of said pot-seal.

This embodiment leads to a compact sealing system. By virtue of its small size, the latter is compatible with many known trocar systems. Since it can be preassembled and easily handled by virtue of this compact structure, it can also be easily fitted into the trocar systems.

In another embodiment of the invention, the distal end of the slats of the expansion cone is connected with a form fit to a socket at the edge of the opening in the seal.

This connection of the distal end of the slats to the socket at the edge of the opening of the seat prevents the slats from slipping during expansion of the seal. This counteracts the possibility of the slats coming loose from the edge and ensures uniform expansion. Moreover, the connection has the effect that, after the removal of a shaft from the trocar, the slats move back to the starting position again together with the sealing opening, on account of the restoring force of the expanded elastic seal.

In one embodiment of the invention, the distal end of the slats of the expansion cone is adhesively bonded to the seal.

Adhesive bonding between the slats and the opening of the seal ensures a non-releasable and secure contact between the components. Undesired separation of the components is thereby avoided, such that the slats are at all times arranged on the opening of the seal. The adhesive bonding is conceivable as a single measure, but also in combination with the form-fit connection.

In another embodiment of the invention, the seal is arranged together with the expansion cone in a casing structure.

The use of a casing structure confers increased stability on the system composed of expansion cone and seal. The assembly composed of the expansion cone, made of stiff material, and of the seal, made of elastic material, forms a structure that is relatively unstable in the lateral direction. This is particularly so to the configuration in which the expansion cone and the seal extend diametrically away from each other starting from their point of connection to each other. An instrument inserted whir a lateral offset or obliquely into the expansion cone would cause a lateral shift or lateral displacement of the assembly. The casing structure counteracts this, but provides a certain degree of flexibility.

In another embodiment of the in vendors, the casing structure is composed of a double ball joint, which is preferably composed of a seal holder, a middle part with ball sections, and a proximal ball socket.

The embodiment of the casing structure as a double ball joint that is movable to a certain degree allows the expansion cone, and fire seal connected to the latter, to execute certain tilting or shifting movements. This is useful particularly for instruments whose shafts have a small diameter. In the case of instruments with thin shafts, they may become offset from the central passage through the opening of the seal. Moreover, particularly in the case of thin flexible shafts, a curved extent of the shaft through, the trocar may arise. Both of these situations nave the effect that the seal does not come uniformly into contact with the shaft about the whole circumference of the latter. The result of this is undesired loss of leaktightness.

By virtue of the casing structure in the form of a double ball joint, the sealing system is able to move such that the shaft once again extends centrally through the opening of the seal. In this way, the desired leaktightness of the trocar system is maintained.

In another embodiment of the invention, the casing structure is composed of a flexible casing tube.

The use of a flexible casing tube also permits very good adaptation of the seal to the offset of an inserted instrument, since such a flexible tube likewise permits a mobility of the sealing system. Adapting the seal to the offset or oblique course of the shad through the opening of the seal likewise ensures the leaktightness of the trocar system.

In another embodiment of the invention, the flexible casing tube is composed of a substantially parallel series of ring elements, wherein two adjacent ring elements are preferably connected to each other at two radially opposite sites, and, furthermore, the sites connecting a ring element to the distally adjacent ring element are in each case always offset by 90° with respect to the connecting sites to the proximally adjacent ring element.

The connecting sites between the ring elements, arranged in a circle shape and alternately offset by 90°, permit a flexibility of the casing lobe in ah lateral directions since, as a result of the connecting sites being arranged radially opposite one another, the connected ring elements have a tilt axis. By means of this, they can be tilted towards one another, born the mutually parallel arrangement, at sites lying circumferentially between the connecting sites. Within the overall arrangement of the ring elements, the 90° offset from one pair to the next pair of ring elements ensures that tilting is possible in two mutually perpendicular directions. That is to say, the casing structure thus formed cars be moved, at its free proximal end in two independent directions and, therefore, in the plane defined by these directions, in addition to the good mobility, and the associated ability to compensate for ah offset of a strait in the trocar, the connecting sites offset by 90° to each other at the same time provide good axial stability since, in the event of loading, the acting forces are distributed uniformly.

A further advantage of using, ring elements is that they are fairly uncomplicated structural components, which simplifies production.

In one embodiment of the invention the connections are flexible webs.

The advantage of this embodiment is that the narrow and therefore flexible webs are arranged directly on the respective elements without multi-part hinges. In this way, the flexible casing tube thereby formed can be produced as a single workpiece, e.g. from plastic, by an injection moulding technique. Since this does away with subsequent assembling of the ring elements, production is very quick and straightforward.

In one embodiment of the invention, the connections are tilting joints.

By constructing the flexible casing tube born individual ring elements and connecting these by means of tilting joints, the length of the flexible casing tube can be varied. In the design of a sealing system, this length can therefore be adapted to the length of the expansion, cone and to the length of the seal. With one type of ring element, it is therefore possible to construct casing tubes of different lengths, which means that this embodiment affords great variability.

In one embodiment of the invention, the ring elements are higher at the sites of a tilting-joint socket than at those of a tilting-joint insert.

The site of the tilting-joint socket in the ring element must have a certain height in order to be able to receive the complete tilting-joint insert. This height is lower at the other parts of the ring element. In this way, the area in which the ring elements can be tilted relative to one another is enlarged, since the distance between the ring elements is greater at the sites lying circumferentially between the tilting joints. In this way, the greatest possible angle of inclination is achieved, which increases the flexibility of the casing tube. As a result, the sealing system can better adapt to any offset of a shaft in the opening of the seal.

In another embodiment of the invention, the flexible casing structure widens conically from the proximal end to the distal end.

By means of this widening, the casing structure is adapted to the difference in cross section between the annular body of the expansion cone and the in most cases greater cross section of the distal end of the seal. This ensures, on the one hand, a good hold on the distal end of the seal and the trocar housing on which the latter is arranged and, on the other hand, on the expansion cone. This leads to the desired stability.

In another embodiment of the invention, the expansion cone is composed of eight to twelve slats, preferably ten slats.

The use of eight to twelve slats, preferably ten slats, permits uniform widening of the opening of the seal, since the number of slats used is such that the gaps arising during widening are as small as possible and, in addition, the distance between two slats in the expanded state is small. Thus, even in the expanded state, a uniform and round shape is still formed by the slats at the opening of the seal. This in particular enhances the leaktightness at the opening of the seal during and after the insertion of a shaft. Moreover, however, these slats also have sufficient stability, since they still have a sufficiently great width. They are therefore not damaged or destroyed by insertion of especially sharp-edged instruments, thereby also providing protection of the seal.

In another embodiment of the invention, the individual slats narrow from the proximal end to the distal end.

In the unexpended state of the expansion cone, the latter should have a surface that is as far as possible closed in order to ensure tied, upon insertion of a shaft, there are no free spares through which the shaft can reach the seal and thus possibly damage the latter. Since a conical structure is present, the circumference at the annular body is much greater than at the level of the opening of the seal. In the case of slats which constantly have the same width along their extent, and in which a closed surface is intended to be present even at the annular body, this has the effect that the slats overlap at the distal end of the expansion cone. This in turn can lead to the slats becoming jammed and thus impeding the function of the expansion cone.

By contrast, the narrowing of the slats means that, in the unexpanded state, there can be no undesired overlapping or jamming of the individual slats. This guarantees the unimpaired functioning of the expansion cone and, despite the continuously decreasing width, an unexpended expansion cone with an almost closed inner surface.

In other embodiments of the invention, the slats, the annular body and the casing structure are made of hard plastic.

In the present case, the use of hard plastic for the slats, the annular body and the casing structure represents a good compromise, since this provides sufficient stability, e.g. during insertion of sharp-edged instruments, but still permits simple production, for example by injection moulding.

In another embodiment of the invention, the seal is made of an elastic material.

The use of an elastic material, for the seal permits suitable widening of the opening of the seal by the expansion cone during insertion of the shaft of an instrument and, at the same time, permits optimal sealing of the shaft of such an instrument, by virtue of the tight contact between elastic material and shaft. This is achieved in particular by the fact that the expanded opening of the seal is pressed against the circumference of the inserted shaft by virtue of the restoring force of the elastic material.

It will be appreciated that the aforementioned features and those still to be explained below can be used not only in the respectively cited combination but also in other combinations or singly, without departing from the scope of the present invention.

BRIEF DESCRIPTION OF THE DRAWINGS

The invention is described and explained in more detail below on the basis of a number of selected illustrative embodiments and with reference to the attached drawings, in which.

DETAILED DESCRIPTION OF PREFERRED EMBODIMENTS

A medical instrument shown in the figures is designated in its entirety by reference number 10.

Figure 1:
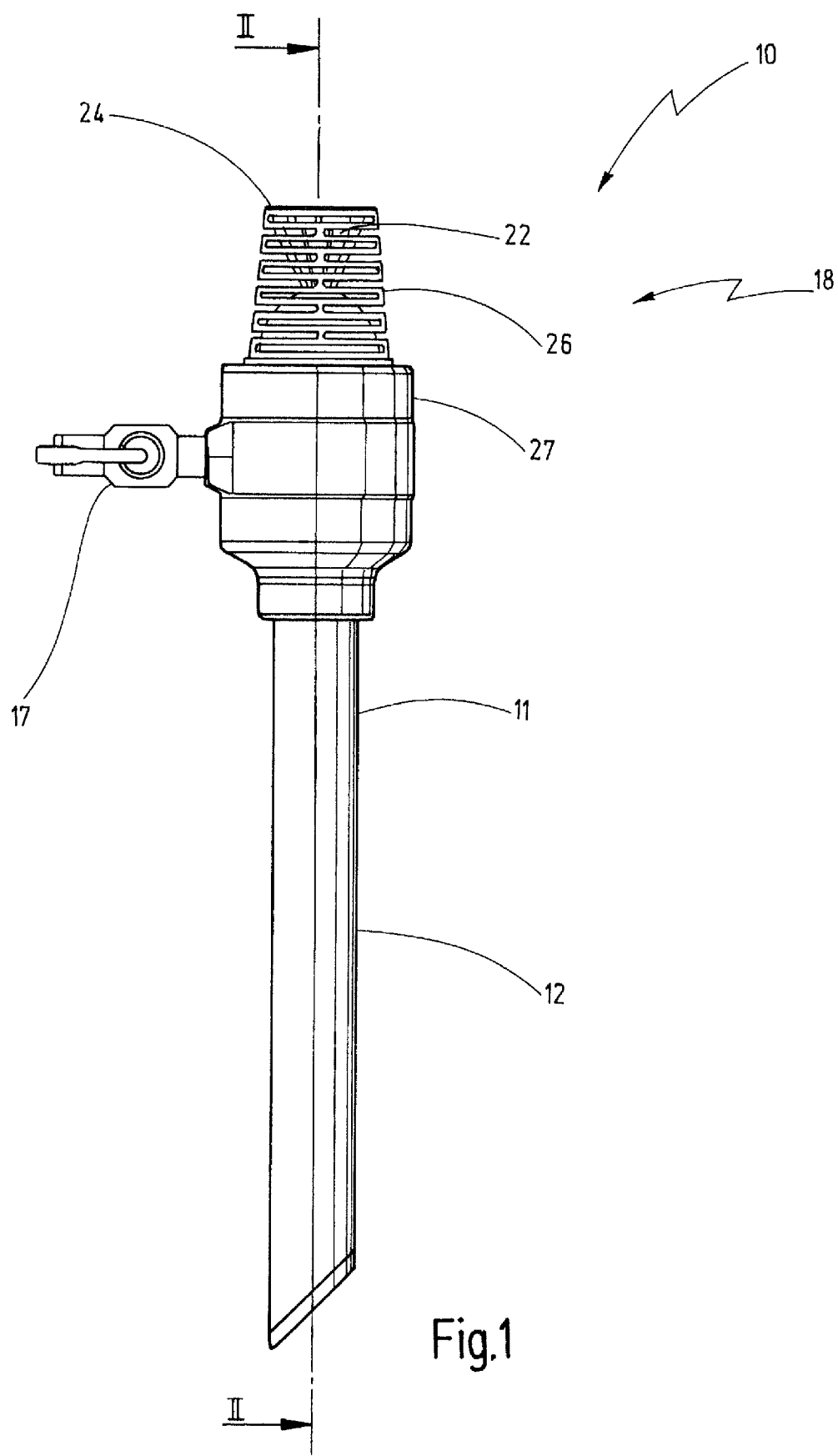
FIG. 1 shows a perspective side view of a medical instrument with a flexible sealing system.
Figure 2:
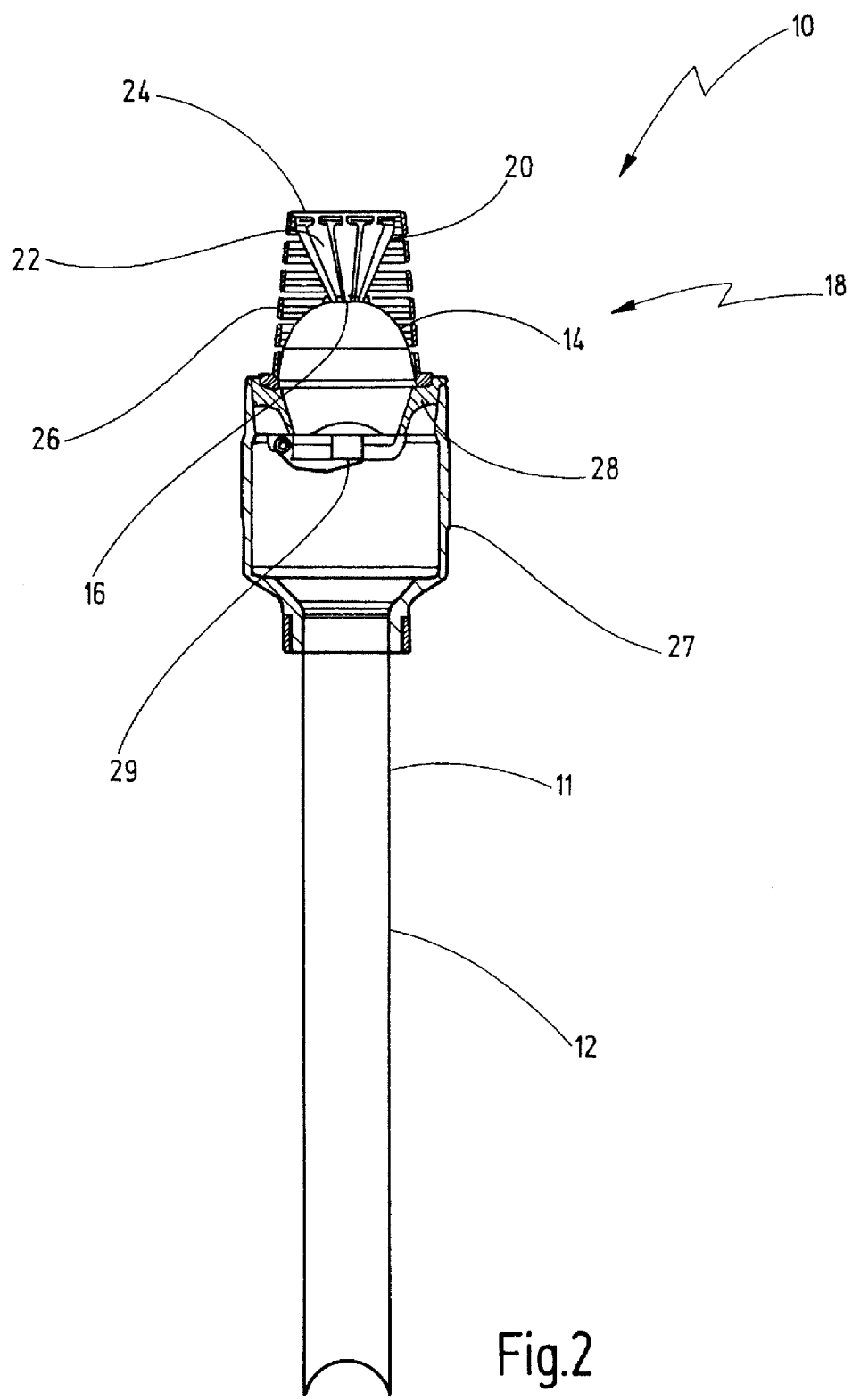
FIG. 2 shows a cross section along the line II-II in FIG. 1.

The medical instrument 10 shown is a trocar and has at its distal end a trocar sleeve 11, formed here by a cannula 12, at its centre a trocar housing 27 and, arranged at the proximal end of the latter, a sealing system 18. FIG. 1 also shows a valve 17, which is arranged on the trocar housing 27 and which can serve, for example, as an admission line for gases. These axe used to perform insufflation of the operating site, in order thereby to obtain better access to the organs, vessels, tissues or the like, on which the operation is to be performed. In order to avoid undesired escape of the gases through the trocar in the proximal direction, a self-closing obturator 29 is arranged in the distal direction from the sealing system 18 (FIG. 2). It closes the proximal opening as soon as there is no shaft inserted into the medical instrument 10.

Figure 5:
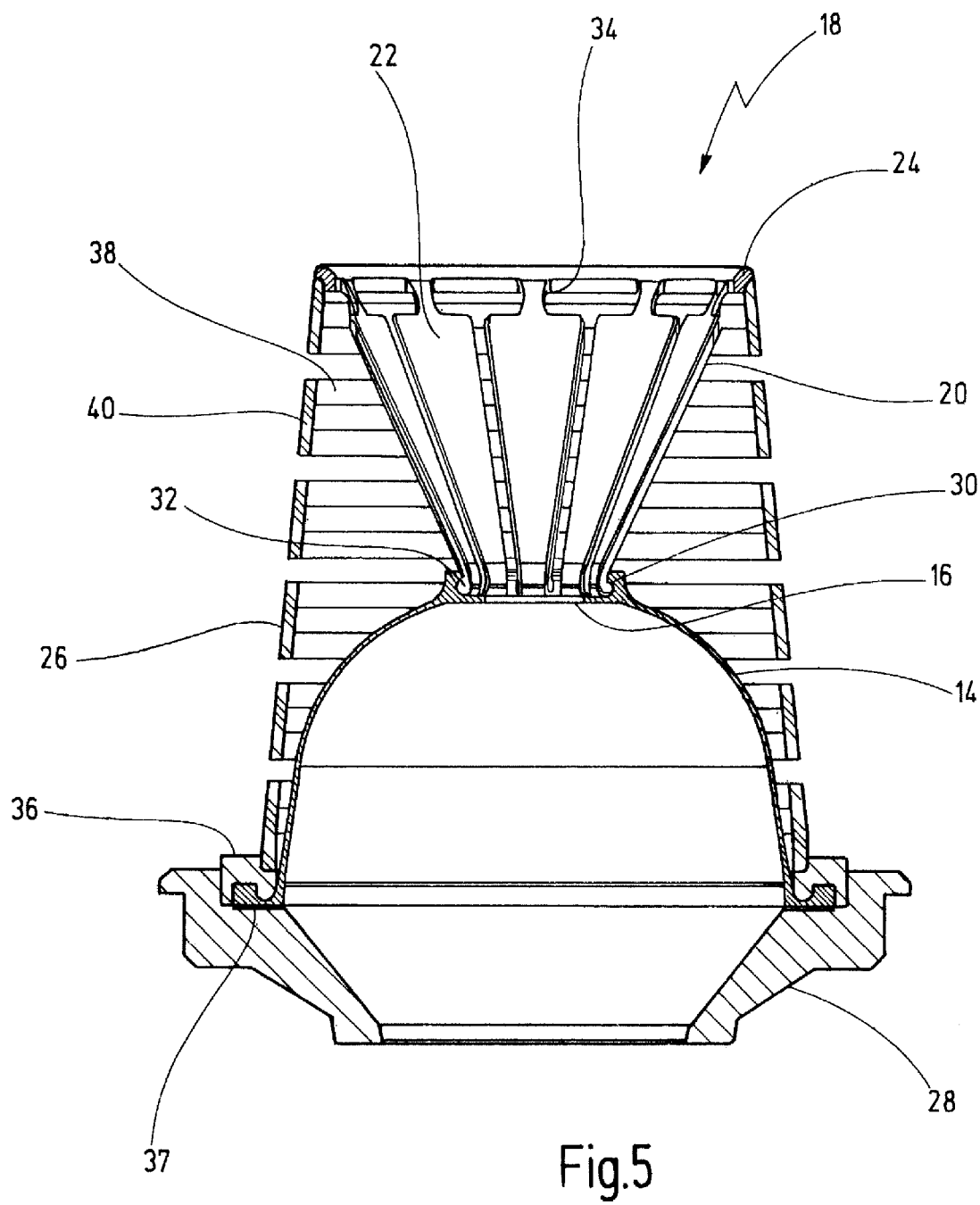
FIG. 5 shows a cross section along the line V-V in FIG. 3.
Figure 7:
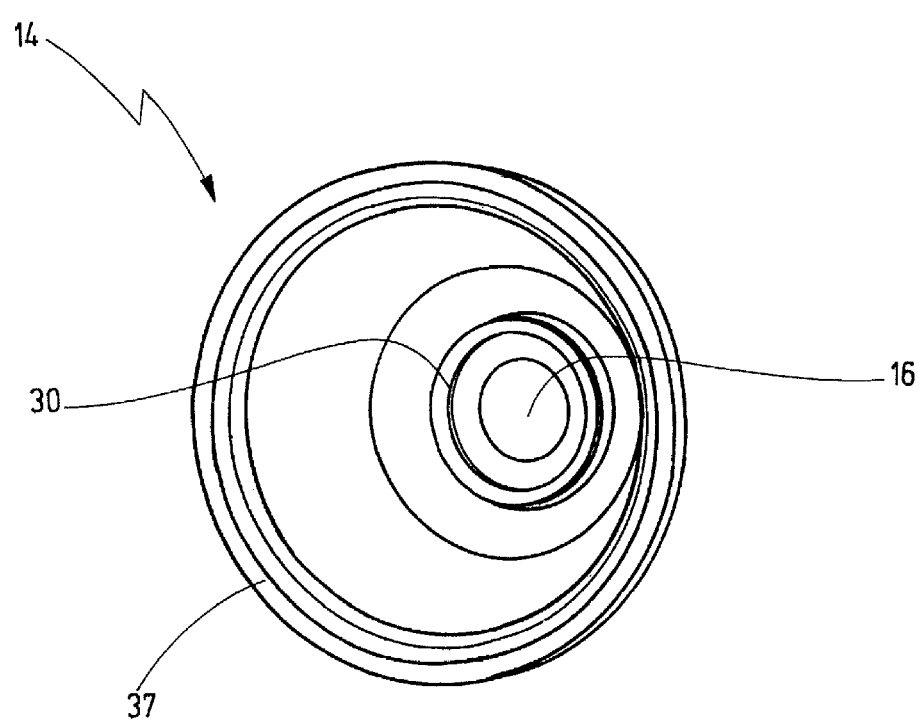
FIG. 7 shows a perspective view of a seal.

As can be seen from FIGS. 1, 2 and 5, the scaling system 18 comprises a seal 14. The seal 14 is designed as a pot-seal. The pot-seal has a peripheral edge designed as a sealing edge. An opening 16 is provided in the bottom area of the pot-seal. The sealing edge 37 of the lade is fastened by a fastening ring 36 to a seal holder 28, with which the sealing system 18 is mounted on the trocar housing 27. The seal 14 extends in the proximal direction away from the seal holder 28 and in so doing narrows. At its proximal end, the seal 14 has a socket 30 that surrounds this opening 16 (FIGS. 5 and 7). An expansion cone 20 is secured on the socket 30 and extends in the proximal direction away from the seal 14 (FIG. 5).

Figure 6:
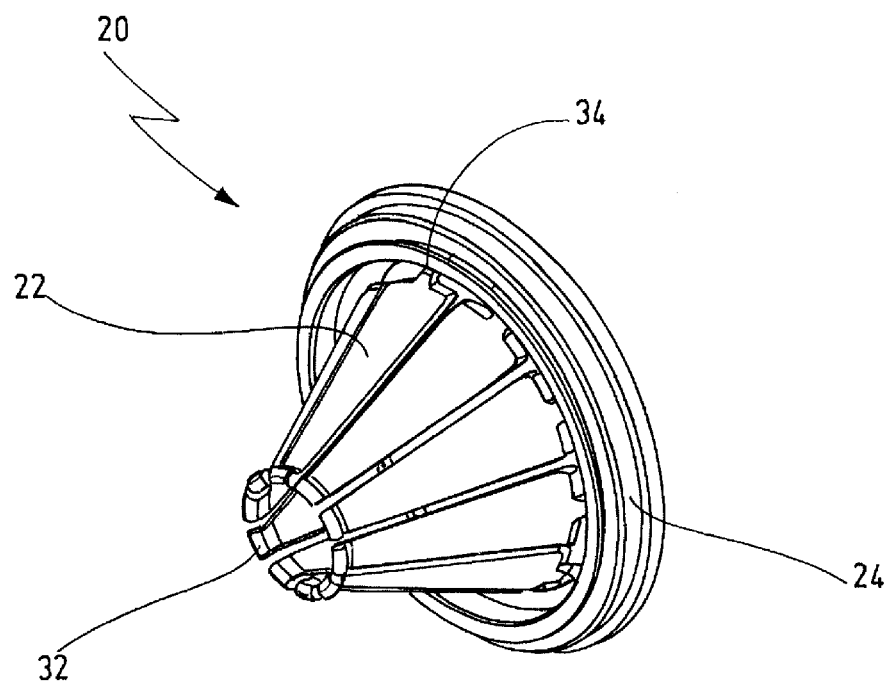
FIG. 6 shows a perspective view of an expansion cone.

As can be seen from FIGS. 5 and 6, this expansion cone 20 is composed of an annular body 24 on which slats 22, oriented in the distal direction, are mounted pivotably by means of film binges 34 in a ring shape. At the distal end, these slats 22 have codpieces 32 that are connected with a form fit to the socket 30 of the seal 14. The expansion cone 20 acquires its corneal shape as a result of the difference in cross section between the annular body 24 and the socket 30. The slats 22 narrow the proximal end to the distal end in such a way as to provide a uniform and almost closed inner surface of the expansion cone 20 in the unexpanded state.

The connection between the slats 22 and the seal 14, wherein the codpieces 32 are fitted in the socket 30, means that when a shaft is inserted, the slats 22 are initially forced radially outwards, as a result of which the opening 16 of the seal 14 is at the same rime expanded, but without being expanded directly by the shaft.

Figure 3:
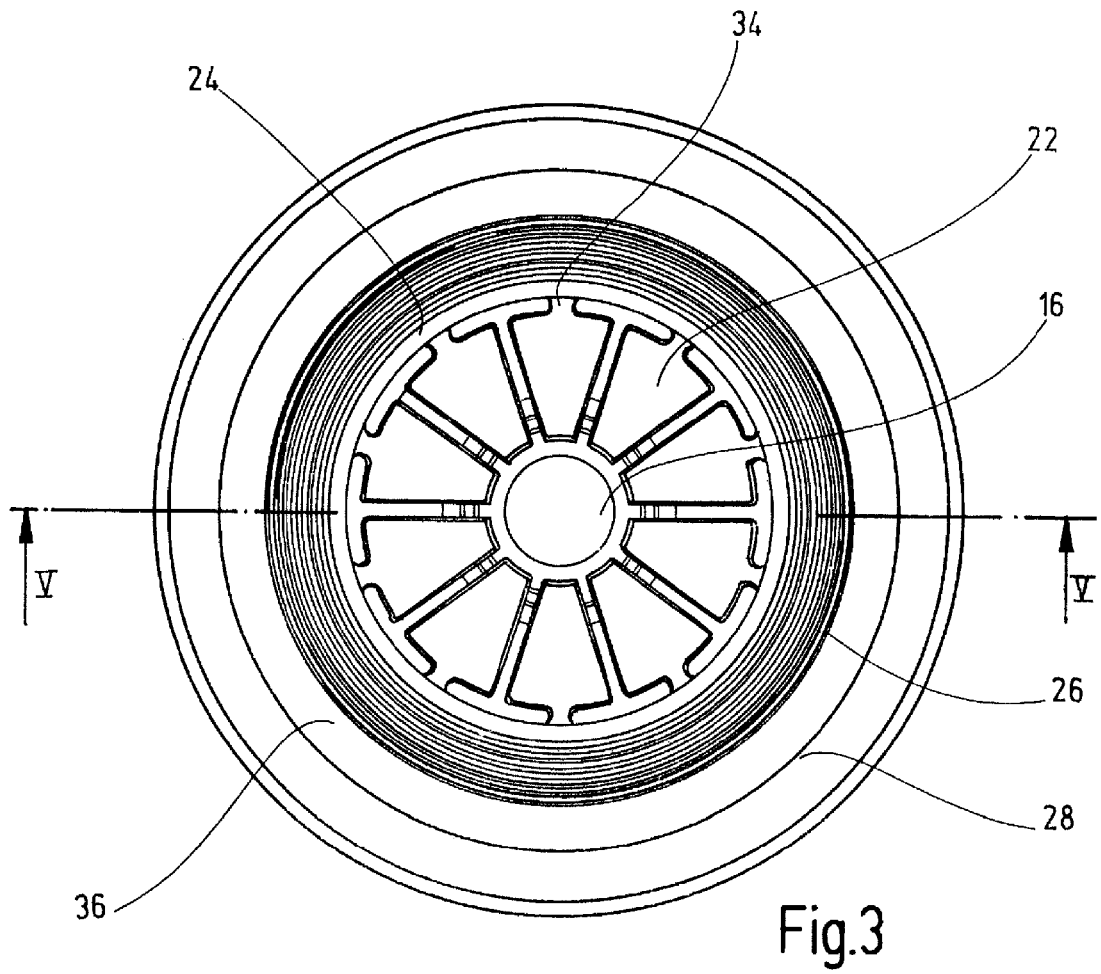
FIG. 3 shows a sealing system of the medical instrument, viewed from the proximal direction.
Figure 4:
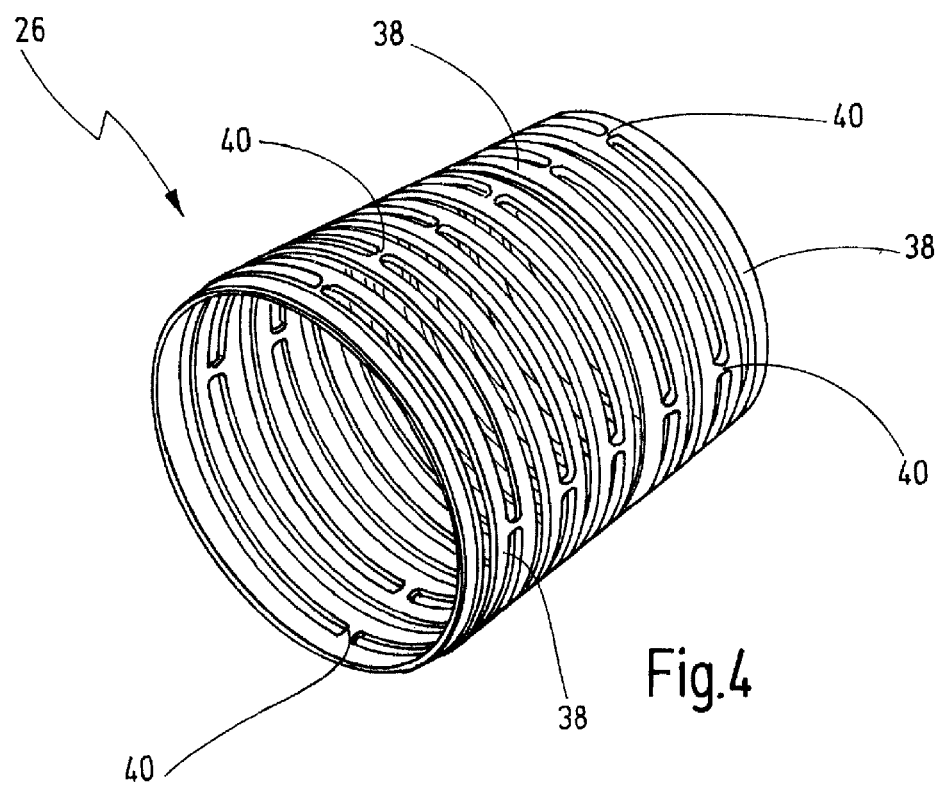
FIG. 4 shows a perspective view of a flexible casing tube of the sealing system.

The assembly of the seal 14 and of die expansion, cone 20 is enclosed by a casing structure designed as a casing tube 26. For this purpose, the casing tube 26 is connected at the distal end to the seal holder 20 and at the proximal end to the annular body 24 (FIG. 3). The casing tube 26 is composed of individual ring elements 38, which are interconnected via webs 40 lying radially opposite each other (FIG. 4). To obtain a flexibility of the casing tube, the latter is made of a sufficiently elastic material, to ensure a flexibility of the webs 40, and the webs 40 are in each case also offset by 90° from one to the next pair of ring elements.

An additional cap (not shown here) having a continuous outer surface can also be arranged around the casing tube 26. In this way, the penetrable casing tube 26 is closed off, such that no contaminants can make their way into and settle within the space between the casing tube 26 and the expansion cone 20 and seal 14.

Figure 8:
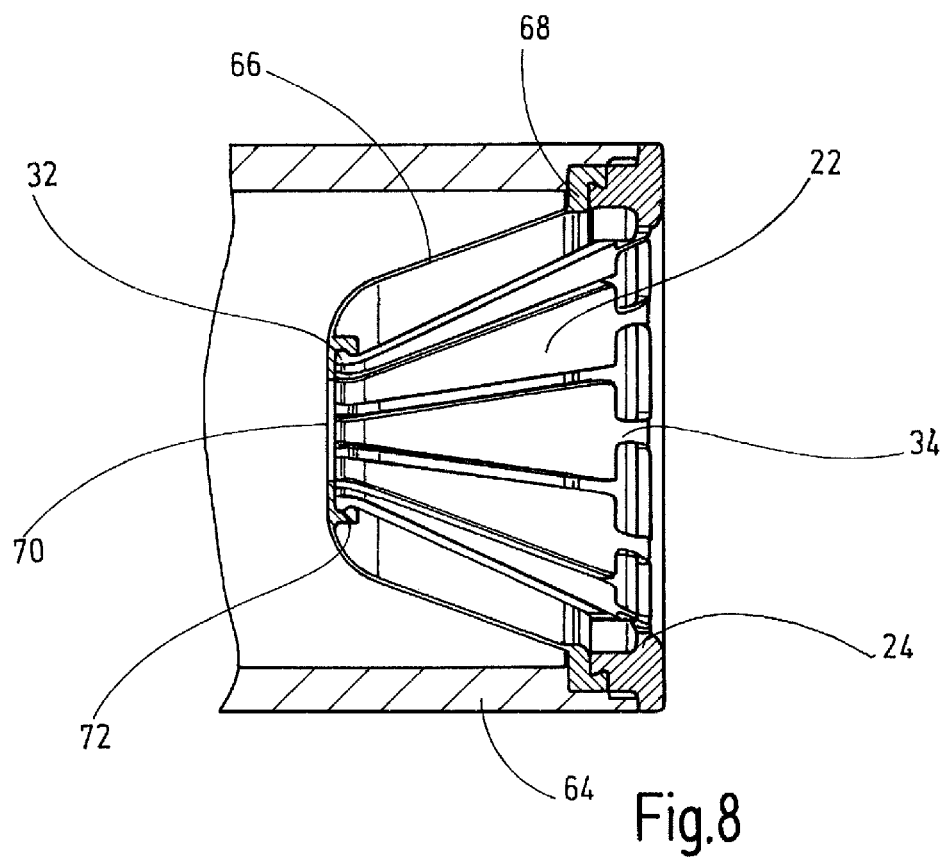
FIG. 8 shows a sectional view of a sealing system in which the seal surrounds the expansion cone.

In contrast to the previously described variant in which the expansion cone 20 extends in the proximal direction away from the proximal end of the seal 14, the pot-seal 66 in the illustrative embodiment in FIG. 8 is arranged such that it narrows from the proximal end to the distal end and in so doing surrounds the expansion cone 20. For this purpose, it is secured by a fastening ring 68 to a trocar housing 64, on which the annular body 24 of the expansion cone 20 is also secured at the proximal end. The distal end of the seal 66 forms an opening 70 surrounded by a socket 72. Analogously to the previously described illustrative embodiment, the end pieces 32 of the slats 22 are arranged with a form fit in the socket 72.

Figure 9:
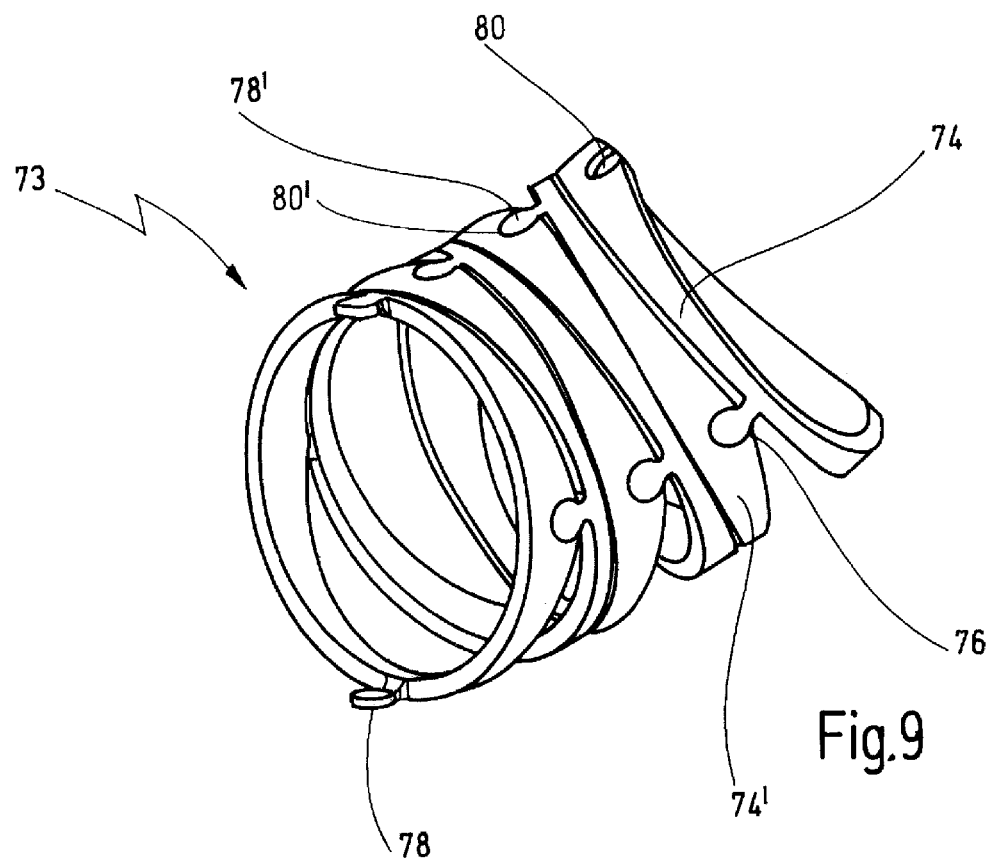
FIG. 9 shows a perspective view of a flexible casing tube with tilting joints.

Another illustrative embodiment of a flexible casing tube is shown in FIG. 9. In contrast to the casing tube 26 shown in FIG. 4, which can be produced as a single part by means of an injection moulding technique, for example, FIG. 9 shows a casing tube 73 composed of separate ring elements 74. These ring elements 74 have two different sides. Whereas one side has two tilting-joint sockets 80, the other side has two tilting-joint inserts 78. The tilting-joint inserts 78 and the tilting-joint sockets 80, respectively, are arranged radially opposite each other. The tilting-joint socket 80 and the tilting-joint insert 78 on one ring element 74 are arranged in a circle and offset by 90° to each other.

As is shown in FIG. 9, several ring elements 74 are interconnected by connection of the tilting-joint inserts 78 of one ring to the tilting-joint sockets 80 of another ring. In this way, the casing tube 73 is formed which, with its connections between the tilting-joint inserts 78 and tilting-joint sockets 80, resembles the webs 40 between the ring elements 38 of the casing tube 26 (FIG. 4 and FIG. 9). The tilting-joint insert 78 and the tilting-joint socket 80 thus form a tilting joint 76, which is responsible for the flexibility of the casing tube 73.

To obtain the greatest possible range of mobility, the ring element 74 is higher at the tilting-joint sockets 80 than at the sites of the tilting-joint insert 78 (FIG. 9). The ring element 74 can thus be pivoted further about the axis formed by the radially opposite tilting joints 76. A first ring element 74 can thus be pivoted, at the site of the tilting-joint socket 80, to a second ring element 74' further than if the latter at the site of the tilting-joint insert 78' were to have the same height as at the site of the tilting joint 76.

Figure 10:
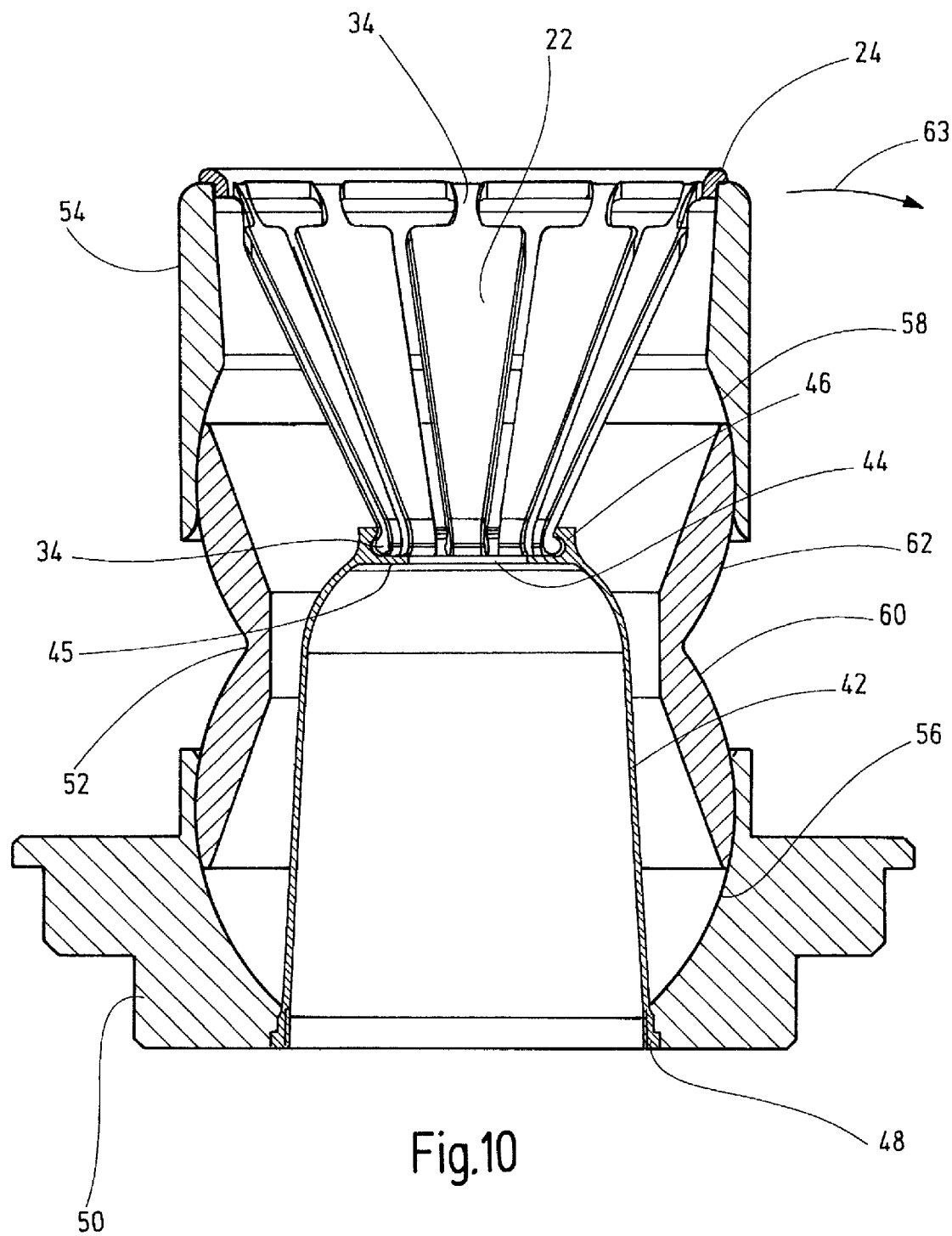
FIG. 10 shows a sectional view of a sealing system with a double ball bearing as a casing structure.

Another illustrative embodiment of a casing structure is shown in FIG. 10.

This casing structure is a double ball joint 41 and is composed of a seal holder 50, a middle part 52 and a ball socket 54. The seal holder 50 has a spherical recess 56 into which the middle part 52 is fitted. For this purpose, the middle part 52 in turn has two ball inserts 60 and 62.

Figure 11:
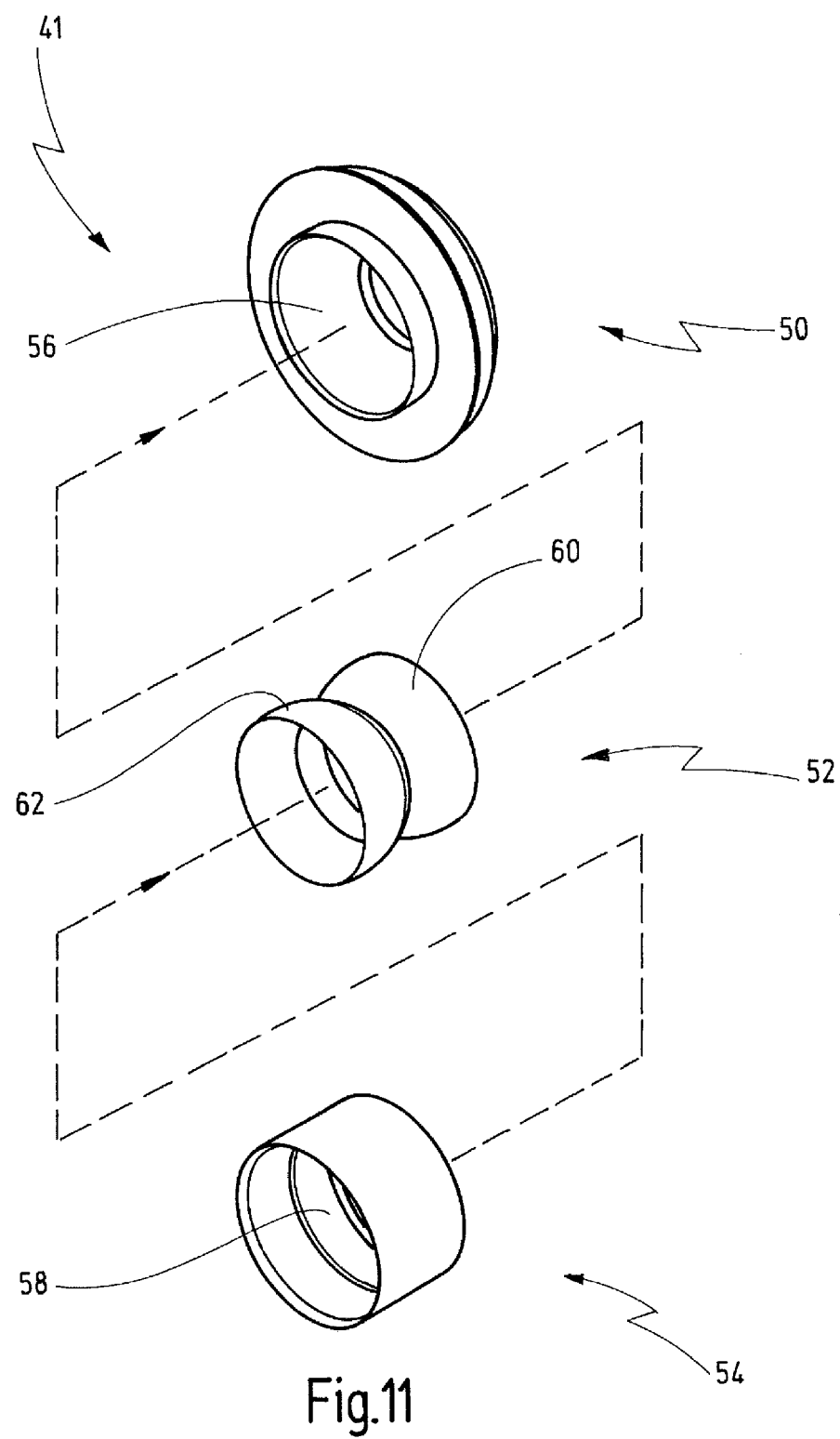
FIG. 11 shows a perspective exploded view of the double ball bearing from FIG. 10.

The ball insert 60 is arranged in the spherical recess 56 and is movable in the latter. The ball socket 54, with a spherical recess 58, is arranged, movably on the proximal end of the ball insert 62 (FIGS. 10 and 11).

This device forms the casing structure for an arrangement of expansion cone 20 and seal 42 comparable to the sealing system 18 from FIG. 5. Here, a sealing edge 48 of the seal 42 is secured on the seal holder 50. At the proximal end, the seal 42 has a socket 46 in which the endpieces 34 of the slats 22 are arranged with a form fit. Moreover, at the proximal end, the seal 42 has an opening 44 and, between the opening 44 and the surrounding socket 46, a sealing lip 45.

The proximal end of the ball socket 54 is connected to the annular body 24 of the expansion cone 20.

Figure 10A:
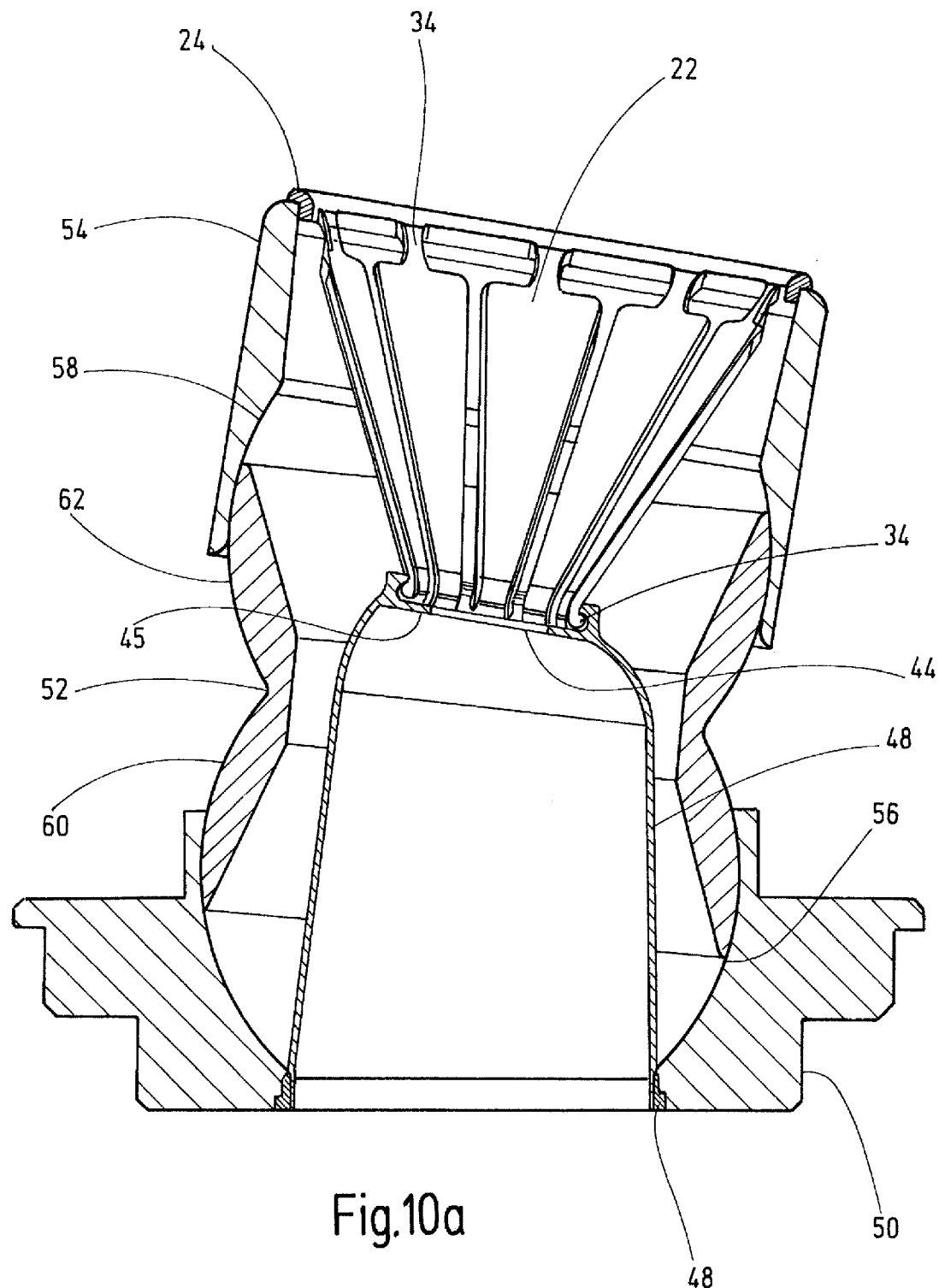
FIG. 10a shows a seating system as in FIG. 10, but with the casing structure deflected.

If a force is applied, to the sealing system in the direction of the arrow 63, for example by the oblique offset of a shaft of smaller cross section, the expansion cone 20 moves along with the shaft in a movable casing body of this hind (FIG. 10a). By means of the movement of the expansion cone 20 in the direction of the arrow 63, the ball socket 54 connected directly thereto is also similarly moved. This is made possible by the ball socket 54 being arranged, pivotably on the middle part 52. The latter in turn also moves to a certain extent, since if is arranged pivotably on the seal holder 50.

During such a movement of the expansion cone 20, the connection between the slats 22 and the socket 46 ensures a corresponding deformation of the seal 48. The result of this is that the shaft, despite the offset, has a central position in the opening 44 of the seal 48 and does not became wedged in the opening 44 and does not cause any loss of leaktightness. By means of the double hall joint 41, the sealing system thus adapts to any offset of a shaft in the medical instrument.

The same also applies to the flexible casing tubes 26 (FIGS. 1-5) and 73 (FIG. 9).

Figure 13:
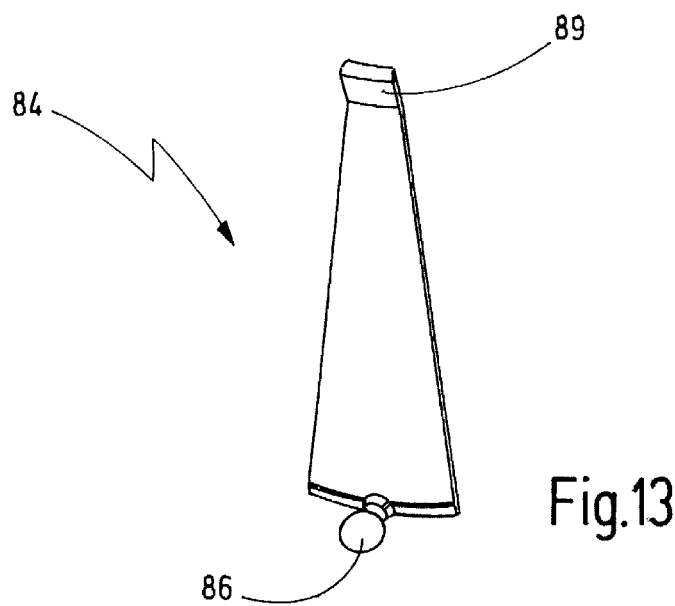
FIG. 13 shows a perspective view of an individual slat comprising a spherical head.

Another illustrative embodiment of slats is shown in FIG. 13. A slat 84 shown there has an endpiece 89 at the second distal end and a spherical head 86 at the first proximal end.

Figure 12:
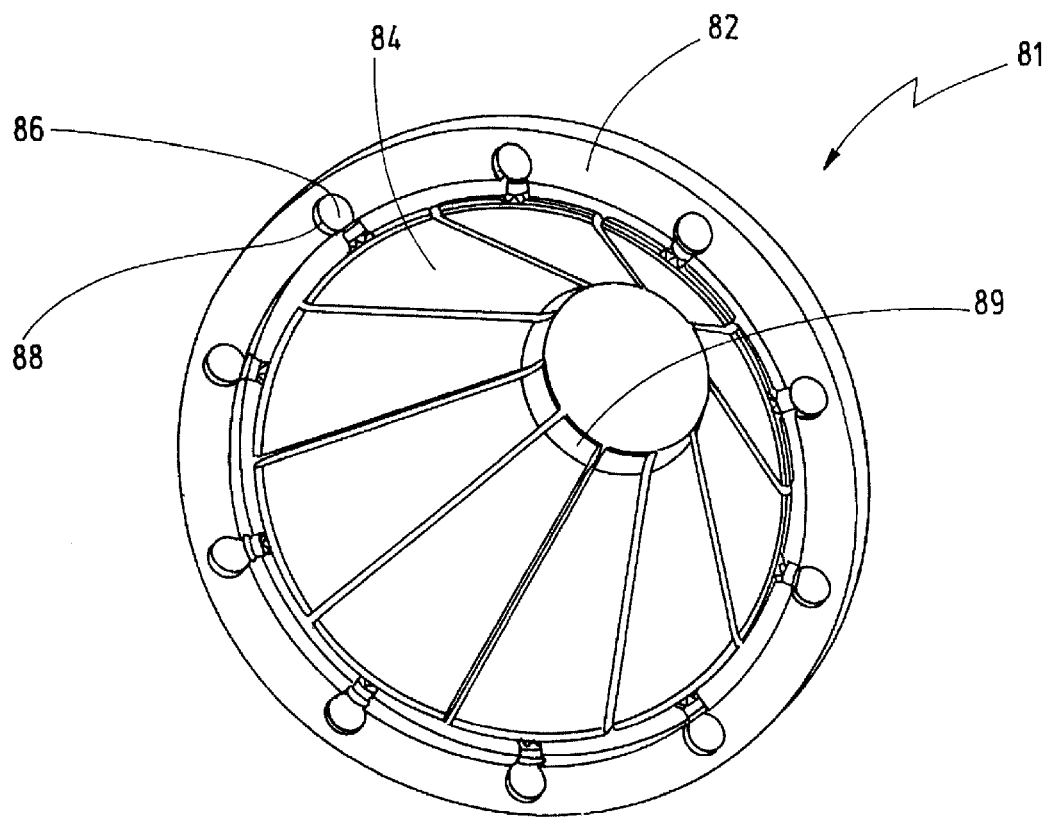
FIG. 12 shows a perspective view of an expansion cone with slats that comprise a spherical head.

This spherical head 86 serves for movable connection of the slat 84 to an annular body 82. For this purpose, the annular body 82 has openings 88 into which dm spherical heads 86 can be inserted. It is conceivable for the slats to be inserted in the mariner of a catch mechanism and also a simple engagement mechanism. For the latter alternative at least, a covet ring (not shown here) would also be required, to prevent the slats 84 from falling out of the annular body 82 (FIG. 12).

In this way, an expansion cone 81 is obtained similar to the expansion cone 20 with the film hinges 34 in the previously mentioned illustrative embodiment. Similarly to the latter, the slats 84 also narrow from the proximal end to the distal end.

Figures 14, 14A:
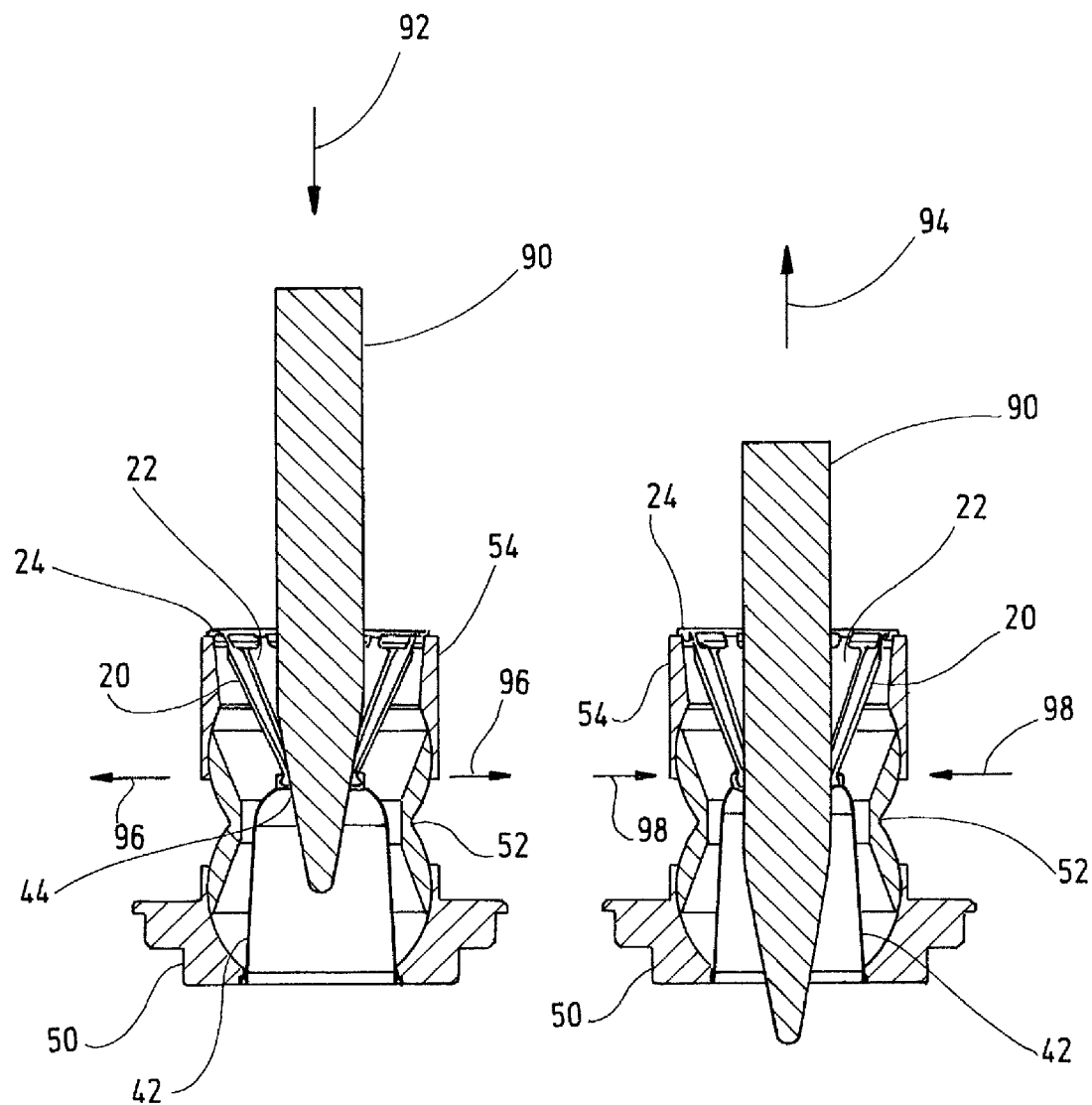
FIG. 14 shows a sectional view of the sealing system with double ball bearing and an applied shaft.
FIG. 14a shows a sectional view of the sealing system with double bad bearing, with the shaft inserted.

The way in which the above-described scaling systems function is now shown, in FIGS. 14 and 14a, taking the example of the sealing system with the double ball joint 41 from FIG. 10.

A shaft 90 is inserted from the proximal direction through the annular body 24 into the sealing system (FIG. 14). This shaft 90 abuts with its distal end against the slats 22 of the expansion cone 20. As it continues to move in the direction indicated by the arrow 92, it is guided in the direction of the opening 44 by the slats 22.

Since the distal end of the shaft 90 tapers to a point, its diameter at the level of the opening 44 increases as it continues to move in the direction indicated by the arrow 92. This has the result that the endpieces 34 of the slats 22 are forced further outwards. This is indicated by the arrows 96. On account of the form-fit connection between the endpieces 34 and the socket 46, the seal 42 is therefore also widened at its opening 44 in the direction indicated by the arrows 96. The widening of the opening 44 by the shaft 90 is thus effected by way of the slats 22.

By virtue of the sealing lip 45 surrounding the opening 44, and of the continuous pressure directed counter to the expansion and provided by the restoring force of the elastic material of the seal 42, the entire system is permanently sealed off during the insertion of the shaft 90, as is shown in FIG. 14.

The state of maximum widening shown in FIG. 14a is reversible in this example by movement of the shaft 90 in the direction indicated by the arrow 94.

By virtue of the restoring force of the elastic material of the seal 42, the latter, as has already been mentioned, exerts a constant pressure on the shaft 90 at the opening 44. When the diameter of the shaft 90 decreases at the level of the opening 44 during the movement in the proximal direction, the diameter of the opening 44 also decreases. This is indicated by the arrows 98. Moreover, because of their connection to the seal 42 via the socket 46, the slats 22 are also pressed against the shaft 90. The slats 22 and the seal 42 thus once again reach their starting position, as can be seen in FIG. 10.

What is claimed is:

1. A medical instrument having a cannula, a seal disposed in said cannula, said seal has an opening for guiding a shaft of another instrument through said seal and said cannula in a sealed manner, an expansion device for expanding said opening in said seal for guiding said shaft of said other instrument of greater diameter in a sealed manner through said expanded opening, said expansion device having an expansion cone comprising a plurality of slats mounted pivotably on an annular body at a first end thereof, a second end of said slats, opposite to said first end, being connected to said seal in an area of said opening, said slats forming said expansion cone narrowing from a proximal to a distal end thereof, wherein said slats are connected at its first ends to said annular body via spherical heads engaging into corresponding openings in said annular body, wherein said second end of said slats of said expansion cone are connected with a form fit to a socket provided at an edge of said opening in said seal.

2. The medical instrument of claim 1, wherein said spherical heads of said slats are held in said annular body by a cover ring.

3. The medical instrument of claim 1, wherein said seal extends in a distal direction away from a distal end of said expansion cone.

4. The medical instrument of claim 3, wherein said seal is designed as a pot-seal a bottom of said pot-seal is connected to said distal end of said expansion cone.

5. The medical instrument of claim 1, wherein said seal surrounds said expansion cone.

6. The medical instrument of claim 5, wherein said seal is designed as a pot-seal, wherein said expansion cone is arranged within said pot-seal, and a distal end of said expansion cone is connected to said opening in a bottom of said pot-seal.

7. The medical instrument of claim 1, wherein said second end of said slats of said expansion cone are adhesively bonded to said seal.

8. The medical instrument of claim 1, wherein said seal together with that expansion cone are arranged in a casing structure.

9. The medical instrument of claim 8, wherein said casing structure is composed of a double ball joint.

10. The medical instrument of claim 9, wherein said double ball joint is composed of a seal holder, a middle part with ball shapes and a proximal ball socket.

11. The medical instrument of claim 8, wherein said casing structure is composed of a flexible casing tube.

12. The medical instrument of claim 11, wherein said flexible casing tube is composed of a series of substantially parallel ring elements.

13. The medical instrument of claim 12, wherein two adjacent ring elements of said series of ring elements are connected to each other at two radially opposite sites.

14. The medical instrument of claim 13, wherein said opposite sites connecting one ring element to a distally adjacent next ring element are in case always offset by 90° with respect to opposite connecting sites to a proximally adjacent next ring element.

15. The medical instrument of claim 13, wherein connections at said connecting sites are designed as flexible webs.

16. The medical instrument of claim 13, wherein connections at said connecting sites are designed as tilting joints.

17. The medical instrument of claim 16, wherein said ring elements having said tilting joints are provided with a tilting joint socket and with a tilting joint insert projecting from that ring into a direction of a tilting-joint socket of an adjacent ring element, said tilting-joint socket of a ring element being provided in an area of a higher height of said ring element and said tilting-joint insert projects from a area of lower height.

18. The medical instrument of claim 11, wherein said flexible casing tube widens conically from a proximal to a distal end thereof.

19. The medical instrument of claim 8, wherein said casing structure is made of a hard plastic.

20. The medical instrument of claim 1, wherein said expansion cone is composed of eight to twelve slats.

21. The medical instrument of claim 1, wherein said expansion cone is composed of ten slats.

22. The medical instrument of claim 1, wherein each individual slat narrows from its first end to its second end.

23. The medical instrument of claim 1, wherein said slats are made of a hard plastic.

24. The medical instrument of claim 1, wherein said annular body is made of a hard plastic.

25. The medical instrument of claim 1, wherein said seal is made of an elastic material.

* * * * *